(12) United States Patent
Siegrist et al.

(10) Patent No.: US 9,141,757 B2
(45) Date of Patent: Sep. 22, 2015

(54) PERFORMANCE DATA USER INTERFACE

(75) Inventors: Rick Siegrist, South Bend, IN (US); Phil Marshall, Portland, OR (US); Daniel Dean, Portland, OR (US); David Potash, South Bend, IN (US); Don Siegrist, Harvard, MA (US); Deirdre Mylod, Granger, IN (US); Dennis Kaldenberg, Granger, IN (US); James Goins, South Bend, IN (US); Jim Strunk, Sellersburg, IN (US); Jim Zeoli, South Bend, IN (US); Araby Thornewill, South Bend, IN (US)

(73) Assignee: Press Ganey Associates, Inc., South Bend, IN (US)

(*) Notice: Subject to any disclaimer, the term of this patent is extended or adjusted under 35 U.S.C. 154(b) by 211 days.

(21) Appl. No.: 13/157,599

(22) Filed: Jun. 10, 2011

(65) Prior Publication Data

US 2012/0117476 A1    May 10, 2012

Related U.S. Application Data

(60) Provisional application No. 61/410,199, filed on Nov. 4, 2010.

(51) Int. Cl.
*G06F 3/00*    (2006.01)
*G06F 19/00*   (2011.01)

(52) U.S. Cl.
CPC .................................. *G06F 19/327* (2013.01)

(58) Field of Classification Search
None
See application file for complete search history.

(56) References Cited

U.S. PATENT DOCUMENTS

| | | | |
|---|---|---|---|
| 2002/0054040 A1* | 5/2002 | Moshal et al. | 345/440 |
| 2006/0041447 A1* | 2/2006 | Vucina et al. | 705/1 |
| 2008/0059292 A1* | 3/2008 | Myers et al. | 705/11 |
| 2009/0063193 A1* | 3/2009 | Barton et al. | 705/3 |
| 2009/0076845 A1* | 3/2009 | Bellin et al. | 705/2 |
| 2009/0228330 A1* | 9/2009 | Karras et al. | 705/10 |
| 2010/0017231 A1* | 1/2010 | Galbraith et al. | 705/3 |
| 2011/0016427 A1* | 1/2011 | Douen | 715/828 |
| 2011/0301977 A1* | 12/2011 | Belcher et al. | 705/3 |

* cited by examiner

*Primary Examiner* — Phenuel Salomon
*Assistant Examiner* — Hua Lu
(74) *Attorney, Agent, or Firm* — Faegre Baker Daniels LLP (57) ABSTRACT

A user interface and methods for providing a user interface comprising graphical representations of data, metrics, and other information specific to a particular user. The data, metrics, and other information may be derived from publically available information, private information, or both.

36 Claims, 6 Drawing Sheets

PERFORMANCE DATA USER INTERFACE

CROSS REFERENCE TO RELATED APPLICATION

The present disclosure claims priority from U.S. provisional application No. 61/410,199, filed Nov. 4, 2010, the disclosure of which is expressly incorporated herein by reference.

FIELD OF THE DISCLOSURE

The present disclosure relates to systems and methods for a user interface. In particular, the present disclosure relates to systems and methods for an interactive user interface having a dashboard appearance. The appearance of the user interface assists healthcare providers in tracking and analyzing comprehensive data sets and also comparing their respective performance against the performance of other healthcare providers.

BACKGROUND OF THE DISCLOSURE

Healthcare providers are constantly looking for ways to improve their clinical, operational, and financial performance. A critical tool in doing so is the ability to efficiently analyze volumes of comprehensive data for each of the foregoing aspects of the healthcare provider's business.

The methods and systems of the present disclosure provide an online, customizable application and interface that allows users to analyze various metrics, optionally including: clinical; operational; financial; and satisfaction metrics. The interface of the present disclosure includes multiple interactive graphical representations, with each representation corresponding to a particular set of data or information.

BRIEF DESCRIPTION OF THE DRAWINGS

The above-mentioned and other features of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several drawings.

DETAILED DESCRIPTION OF THE DISCLOSURE

The embodiments disclosed herein are not intended to be exhaustive or limit the disclosure to the precise forms disclosed in the following detailed description. Rather, the embodiments are chosen and described so that others skilled in the art may utilize their teachings.

In operation, a user of the systems and methods of the present disclosure will begin by using hardware capable of establishing and maintaining an internet connection, such as a desktop or handheld computer, to login to a secure website using a given username and password. In one embodiment, the user may choose his or her username and password. Upon acceptance of the username and password, an interface will appear similar to the screenshot shown in FIG. 1.

In one embodiment, the user may be required to login to the network of the administrator of the methods and systems of the present disclosure. Once logged in, the user's computer may communicate with a server that stores data and/or memory necessary during use of the systems and methods of the present disclosure. The terms "network," "local area network," "LAN," "wide area network," or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. The computers, or other computers, termed "workstations," provide a user interface so that users of computer networks can access the network resources, e.g., shared data files. The computers have at least one processor for executing machine instructions, and memory for storing instructions and other information. Many combinations of processing circuitry and information storing equipment are known by those of ordinary skill in these arts. A processor may be a microprocessor, a digital signal processor ("DSP"), a central processing unit ("CPU"), or other circuit or equivalent capable of interpreting instructions or performing logical actions on information. Memory includes both volatile and non-volatile memory, including temporary and cache, in electronic, magnetic, optical, printed, or other format used to store information. Users activate computer programs and/or network resources to create "processes" which include both the general operation of the computer program along with specific operating characteristics determined by input variables and its environment.

Additionally, reference to a user profile or end-user profile in the present disclosure should be understood to refer to a common profile context that governs the user's experience while using the methods and systems of the present disclosure. A user's profile is unique to a particular user, and in an exemplary embodiment, is designed to allow the user to review particular aspects of the user's company's or organization's data. That is, the term "user" refers to a live person who is using the methods and systems of the present disclosure to view data associated with the user's company or organization. For example, a doctor may be a "user" and that doctor's hospital may be a "company" or "organization." In an exemplary embodiment, the user's profile is comprised of pre-defined (static) and dynamic (real-time) attributes, including client-specific, end-user specific, data view, time period, and application-specific attributes, all intended to assist the user in achieving a personalized experience while simultaneously enforcing any authorization privileges put in place by the user's company or organization. In operation, the systems and methods of the present disclosure may query, or, via SSO (single sign on), be informed about the current state of the user's profile and accordingly enforce authorization privileges defined within the user's profile.

Figure 1:
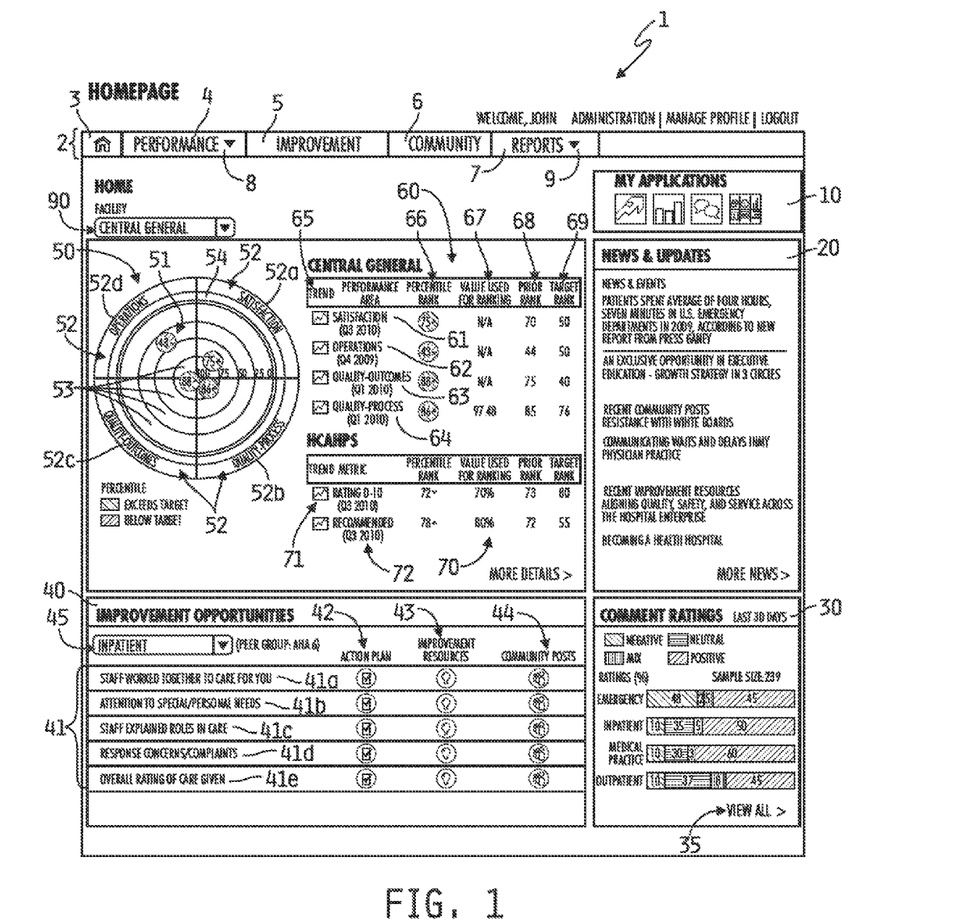
FIG. 1 depicts a screenshot of an exemplary homepage.

With the above general understanding, FIG. 1 displays a screenshot of the Homepage 1 for the interface. Homepage 1 includes several interactive areas and/or clickable icons that, upon selection using hardware such as a mouse, will direct the user to a separate screen. For example, navigation bar 2 includes several tabs, including a home icon 3 which directs a user to the screenshot that is displayed as FIG. 1, a "Performance" tab 4, an "Improvement" tab 5, a "Community" tab 6, and a "Reports" tab 7. A Performance Drop Down 8 and a Reports Drop Down 9 also are included. In one embodiment, selection of any of the foregoing tabs or choices in a drop down will direct the user to a different screen on which additional interactive areas or icons may appear. In addition, it should be understood that some destinations may be rendered in a different browser session while other destinations may be rendered in the same browser session as Homepage 1.

Homepage 1 also includes Dataview Dropdown 90. Dataview Dropdown 90 allows the user to select how he wishes to review data for his company or organization. In this exemplary embodiment, the user has selected a particular location of his organization (the "Central General" facility). Since Dropdown 90 is integrated with the remaining icons and applications in the methods and systems of the present disclosure, the user's selection in Dropdown 90 controls what data appears in those areas and applications. It should be understood that the selection of only a single facility as shown in this embodiment is exemplary only. In another exemplary embodiment, the user may select an option in Dropdown 90 facilities for which he has permission to view.

Referring still to FIG. 1, multiple interactive areas, or icons, are also displayed. It should be understood that the terms "interactive area" and "icon" may be used interchangeably throughout the present disclosure. While the user may tailor the homepage to include different varieties of areas/icons, several exemplary areas are provided in FIG. 1, including: a "My Applications" area 10; a "News and Updates" area 20; a "Comment Ratings" area 30; an "Improvement Opportunities" area 40; a dart chart graphical representation area 50; a performance chart graphical representation area 60; and an HCAHPS area 70. Note that, depending upon the user's selection in Dataview Drop Down 90, a variety of CAHPS data may be displayed in HCAHPS area 70, including, for example, data related to home and health CAHPS (HH-CAHPS), or clinician and group CAHPS data (CG-CAHPS). As discussed in more detail below, many of the customizable areas/icons are a representation of specific sets of data, including, optionally, both data from publically available sources and data stored in a proprietary database or databases.

"My Applications" icon 10 allows a user to view his assigned applications based on his subscription, which is defined in the user's profile. Since many icons are tied to specific data, the user can select the respective application according to their particular interest at the time.

"News and Updates" 20 provides the user with a quick reference to publically available news and information, such as, for example, news stories from the Associated Press. In one embodiment, the news and information associated with icon 20 is customized according to the user's profile. Thus, if the user is a home healthcare provider, the user may see news stories in the field of home healthcare services. In addition, the administrator of the methods and systems of the present disclosure may alert the user to new resources, improvements to existing resources or relevant comments posted by industry peers. Thus, icon 20 may provide a user with specific news and information relevant to its operations as well as additional resources available through the methods and systems of the present disclosure. It should be understood that the information provided in "News and Updates" 20 may be provided as clickable links, or "hotlinks," as the term is generally understood. Each individual news story or update may be a separate hotlink.

"Comment Ratings" 30 allows a user to quickly review the types of comments made about his company or organization, including positive, neutral, and negative comments. In addition, the user may choose to review the actual comments by clicking on the "View All" hotlink 35. As shown in FIG. 1, in this embodiment, the comments are color-coded percentages of the comments received. For example, many users of the systems and method of the present disclosure may be healthcare providers that send surveys to their patients. Icon 30 allows the user to quickly analyze the comments made by those patients who responded to the survey. In this exemplary embodiment, icon 30 allows a user to review comments based on the type of respondent—e.g., outpatients, inpatients, etc. Thus, by providing a quick reference guide that is color-coded and percentage-based, users can achieve a quick understanding of the experiences of patients or other type of clients with the user.

Figure 5A:
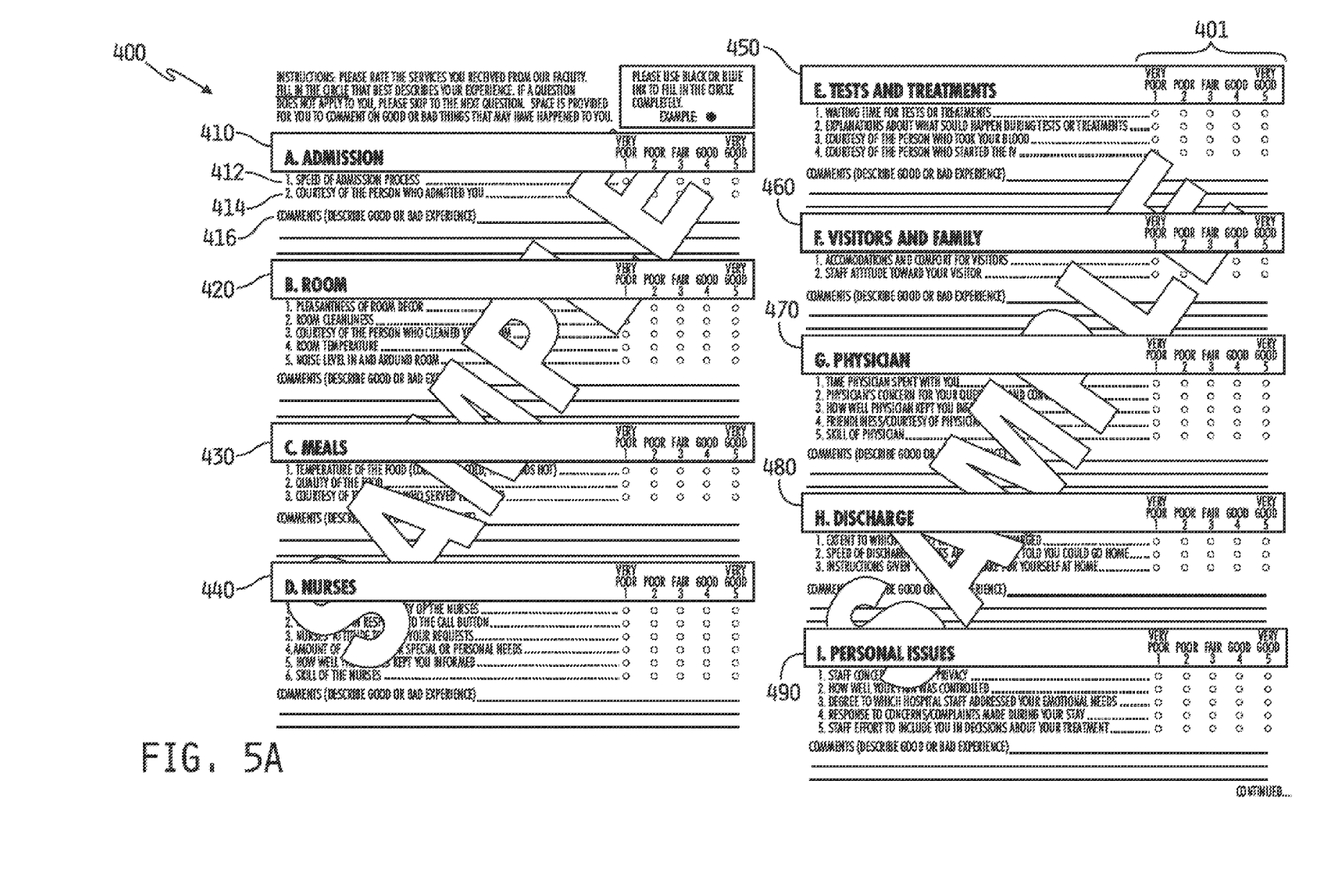
FIGS. 5A and 5B depict an exemplary survey used for compiling inpatient data.
Figure 5B:
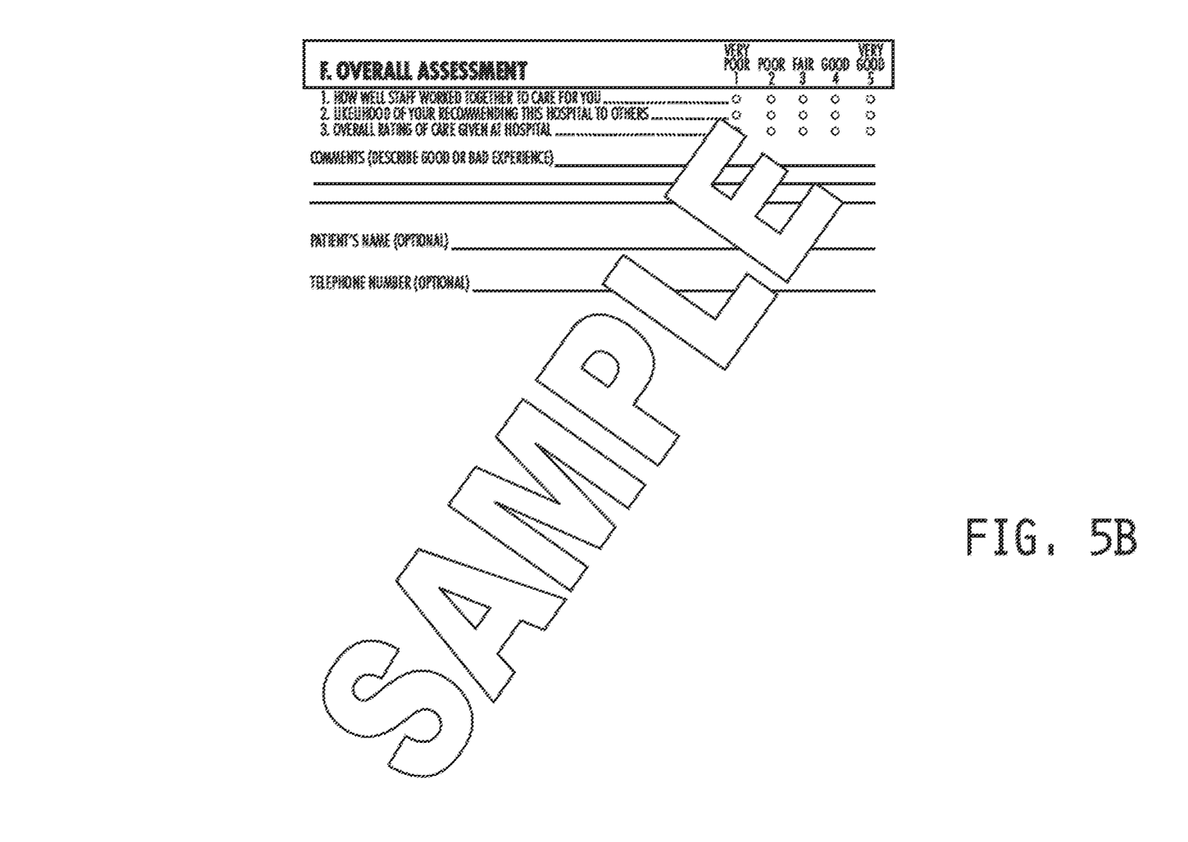

"Improvement Opportunities" 40 allows a user to quickly access suggested improvement opportunities and to receive advice on how to achieve the suggested improvement. And as shown in FIG. 1, in this embodiment, 40 allows a user to access different types of information and different types of suggestions for each respective opportunity, with each being represented by a separate icon. Dropdown 45 may allow a user to select a specific service for which he wants to review his company's or organizations performance. That is, drop down 45 lists various service areas that correspond to the services provided by the owner or administrator of the methods and systems of the present disclosure. For instance, if the user's company or organization is a hospital, the owner or administrator may provide surveys to the user's clients. The types of surveys each represent a different service, and each may be selected from drop down 45. In this exemplary embodiment, the use selected to review inpatient performance and thus to focus on improvement opportunities related to that specific area of his company or organization. The user may also be able to choose other categories from drop down 45, such as outpatient, or operations, etc. Once the type of service is chosen, the user can then view specific categories 41 where improvement may be needed, with each category 41*a-e* corresponding to questions from surveys related to the type of service chosen. For example, if the user chooses "Inpatient," then the categories for improvement will match questions from a section of the Inpatient Survey entitled "Overall Assessment," as shown in FIG. 5B. In this embodiment, five categories of survey information 41*a-e* are provided: "Staff worked together for you" 41*a*; "Attention to special/personal needs" 41*b*; "Staff explained roles in care" 41*c*; "Response concerns/complaints" 41*d*; and "Overall rating of care given" 41*e*. It should be understood that these five categories are exemplary only, and that additional and/or different categories may be included. Each category of survey information is a summary of survey responses received for the specific user. In an exemplary embodiment, the data tied to a chosen category from drop down 45 may be private data, i.e., proprietary data of the administrator of the methods and systems of the present disclosure, or publically available data, or both.

For each of these categories 41, three separate and distinct icons can be selected by the user: "Action Plan" 42; "Improvement Resources" 43; and "Community Posts" 44. In this embodiment, clicking on "Action Plan" 42 will open a new screen that provides the user with steps for improving the client's experience relative to the category selected. Optionally, "Action Plan" 42 may also include a summary of the survey data for the category selected. Thus, for example, if the user selected "Action Plan" 42 for "Staff explained roles in care" 41*c*, a new screen would appear, and the screen would include text and/or graphical representations that summarize survey data and suggest action steps for improving patient response according to that data. The user would have a similar experience by clicking on either "Improvement Resources"

43 or "Community Posts" 44 except for the difference in the text and/or graphical representations that appear. For example, "Improvement Resources" 43 will provide the user with resources he can use to help him accomplish the steps provided in "Action Plan" 42.

Referring still to FIG. 1, dart chart 50 provides the user with a graphical representation of their performance across various categories. Dart chart 50 and performance chart 60 are related. Essentially, dart chart 50 is a graphical representation of the percentile ranks shown in performance chart 60. As such, dart chart 50 is designed to look like a dartboard, which, in combination with the circular representations 51 shown in each quadrant of chart 50—each circle 51 being designed to look like darts on a dartboard—allows the user to quickly access his performance in the designated categories.

In this exemplary embodiment, dart chart 50 is divided into four quadrants 52, four quartiles 53, and an outer ring 54 that is color coded according to the user's predetermined target performance. In this embodiment, the four quadrants 52 include: the "Satisfaction" quadrant 52a; the "Quality-Processes" quadrant 52b; the "Quality-Outcomes" quadrant 52c; and the "Operations" quadrant 52d. Each quadrant also includes a circular representation 51. Each circular representation 51 includes a number which represents the organization's performance in terms of an average of the percentile ranks of the quadrants respective component percentile ranks relative to similar entities. The average percentile rank is located in the performance chart 60 on the homepage 1—calculation of the percentile rank is discussed in more detail below. Thus, for example, circle 51 in "Satisfaction" quadrant 52a indicates the organization performed better than seventy four percent of the entities to which it is being compared. In addition, the placement of each circle 51 within each quadrant 52 also corresponds to the quartiles 53. Starting toward the outer edge of dart chart and moving inward, each quartile 53 is represented by a different shade (e.g., light gray or dark gray) and a number, 0, 25, 50, or 100. Thus, for example, in "Quality-Outcomes" quadrant 52c, the organization received a percentile rank of 88. Because this percentile rank is between 75 and 100, circle 51 in quadrant 52c falls within the innermost quartile (i.e., closest to what looks like the traditional bull's-eye on a dartboard).

In addition, each circular representation 51 is color-coded. In one embodiment, circles 51 may be color-coded according to an established target value for a given performance area (target values are discussed in more detail below). When target values exist, the color-coding of each circular representation 51 reflects how the user performed relative to their selected target value. For example, green may equate to exceeding the user's target range, while red may indicate that the user was below target. In yet another exemplary embodiment, three colors may be used, with, for example, yellow indicating the user was within a pre-defined range of the target value. The colors chosen in the foregoing description are exemplary only, as any color scheme may be selected. Outer ring 54 is also color-coded with the same color scheme as circles 51. Accordingly, the color of outer ring 54 for each quadrant 52a-d will correspond with the color of the circle 51 that falls within that same quadrant. Thus, circles 51, outer ring 54, the general dartboard design, and the color scheme associated with the same, all provide a user with multiple visual cues for quickly assessing, at a high level, his performance for each category.

Referring still to FIG. 1, in this exemplary embodiment, performance chart 60 provides a summary of the data for four separate top-level metrics, including: the "Satisfaction" metric 61; the "Operations" metric 62; the "Quality-Outcomes" metric 63 and the "Quality-Process" metric 64. Data for the Satisfaction metric 61 is drawn either from the organization's most recent data with the administrator of the methods and systems of the present disclosure or from publically available CAHPS data (discussed in more detail below). Data for the Operations metric 62 is drawn from the most recent annual MedPAR (Medicare Provider Analysis and Review) file, with case detail on all Medicare acute care hospital discharges including ALOS (Average Length of Stay) and costs. Data for the Quality-Process metric 63 is drawn from the reporting of clinical performance data related to specific disease related groups as prescribed by the Center for Medicare/Medicaid Services. Data for the Quality—Outcomes metric 64 is also drawn from MedPAR. Each of the foregoing metrics is clickable, i.e., a hotlink. In addition, these four metrics 61, 62, 63, and 64 correspond directly to the four quadrants 52a-d in dart chart 50, and in this embodiment, the same color scheme used for circles 51 and outer ring 54 is also used to illustrate the percentile rank 66 for each metric 61, 62, 63, 64. Thus, performance chart 60 complements dart chart 50 and provides a summary of the data values used to establish the percentile rank 66. These values and the calculations used to determine the same will be discussed in more detail below.

In this exemplary embodiment, performance chart 60 provides aggregate data for the first quarter of 2010. The time period used for performance chart 60, and thus dart chart 50, can be varied by the administrator of the disclosed system and a quartile system is to be understood as exemplary only. Within performance chart 60 are additional graphical representations and data values corresponding to each metric, including: the "Trend" icon 65; the "Percentile Rank" 66; the "Value Used for Ranking" 67; the "Prior Rank" 68; and the "Target Rank" 69.

If a user selects the Trend icon 65 for a particular metric, a screen will appear that includes a graphical representation of the data used to calculate the percentile rank for that metric. The time periods that appear on the trend graphic will depend on which time periods are available, with a maximum of five time periods shown when a quarterly time period applies and a maximum of 13 time periods when a monthly time period applies. In addition, if a user clicks trend icon 65, the graph that appears may reflect public and/or private data. If private data is shown, the time periods may be quarterly, for example. On the other hand, if public data is used for trend icon 65, the time periods may be annual. These time periods, however, are exemplary only. Trend icon 65 and the graphics that appear if a user clicks the same are discussed in more detail below with reference to FIGS. 3 and 4.

The "Percentile Rank" 66 is the user's rank, on a metric-by-metric basis, in comparison to its peers/other organizations for the same metric, and is based on data collected on a nationwide basis—including data collected from both public and private sources. Additionally, the organization's Percentile Rank is directly related to the Value Used for Ranking 67 for each metric, which itself is calculated based on specific data—including public data, private data, and also survey data. That is, the Value Used for Ranking 67 ultimately dictates the organization's percentile rank for a given metric. In FIG. 1, the Percentile Rank 66 for each metric is the aggregate of the percentile ranks for each survey or dataset used in that given metric—these surveys, datasets, and the calculations for Percentile Rank 66 and Value Used for Ranking 67 are discussed in more detail below.

Referring still to FIG. 1, the Percentile Rank 66 for each respective metric corresponds directly to the dart chart 50. The circles associated with each percentile rank are also color-coded the same as what appears in dart chart 50. Thus, the percentile rank for each metric as displayed in performance chart 60 is the same value that appears in the corresponding quadrant 52 for that metric in dart chart 50. As an additional cue for the user, arrows 80 are provided next to each circle in both the dart chart 50 and the performance chart 60 indicate whether the organization's current rank reflects an increase or decrease in rank relative to the organization's prior rank. The data is used to calculate the number that appears in the "Value Used for Ranking" 67 column, and then that Value 67 is used to calculate the percentile rank. The Value Used for Ranking metric 67, and the calculations used to determine the same, is discussed in more detail below.

"Prior Rank" 68 reflects an organization's value from a previous time period. The time period for which the value is determined depends on the type of data available, and thus could be weekly, monthly, quarterly, annually, etc. The Prior Rank 68 for each metric is compared to the current Percentile Rank 66 for each metric in order to determine whether the organization improved or worsened its performance, as reflected by arrows 80.

As referenced above, for some performance areas, users may select a target value; this is reflected in the "Target Rank" column 69. Target Rank 69 tells the user what target percentile rank the organization was pursuing for the given time period. Any color-coding of an organization's aggregate Percentile Rank 66 is determined by comparing the same to the organization's Target Rank 69 for a given metric.

With still further reference to FIG. 1, the HCAHPS area 70 is also provided. HCAHPS 70 functions very similar to performance chart 60, except that instead of several metrics, it provides for two performance areas—Ratings 71 and Recommended 72. In an exemplary embodiment, the data represented in areas 71 and 72 may be proprietary data of the administrator of the methods and systems of the present disclosure, publically available data, or both. Ratings 71 is based on the percentage of respondents who rated a facility/healthcare provider with a top rating of 9-10. Recommended 72 is based on the percentage of respondents who have a strong likelihood to recommend a facility/healthcare provider. It should be understood that HCAHPS 70 may be either HCAHPS, HHCAHPS, CGCAHPS, or merely CAHPS. This is an acronym for the Consumer Assessment of Healthcare Providers and Systems, which is a government required survey instrument. HCAHPS can be used as a method for calculating Satisfaction. Indeed, in this embodiment, HCAHPS 70 is the default setting; however, administrators may also choose to use data and survey scores from the administrator of the method and systems of the present disclosure. The time period applicable to either the public CAHPS or the administrator's CAHPS may also be different. For example, the administrator may calculate CAHPS on a monthly basis and the public CAHPS may be calculated on an annual basis. It should be understood that these time periods are exemplary only, and thus should not be interpreted to limit any CAHPS calculations.

Figure 2:
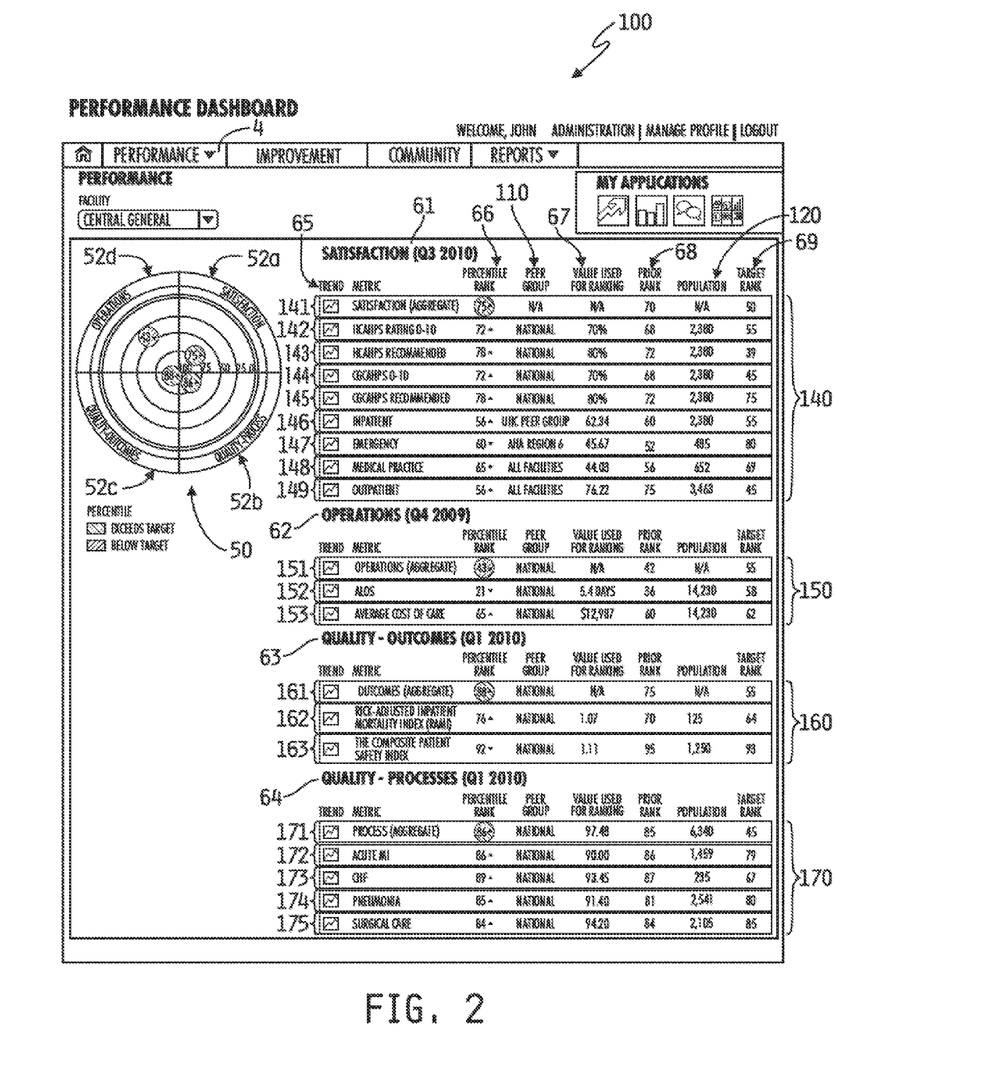
FIG. 2 depicts a screenshot of an exemplary performance dashboard.

Referring now to FIG. 2, by selecting the "Performance" tab 4, a user will be sent to a new webpage, shown here as "Performance Dashboard" 100. As can be seen by comparing FIG. 1 and FIG. 2, Dashboard 100 corresponds to, but also expands on the Homepage 1 in FIG. 1. Specifically, Dashboard 100 still shows metrics for Satisfaction 61, Operations 62, Quality-Process 63 and Quality-Outcomes 64, and these are also clickable hotlinks that, if chosen, will take the user to yet another webpage. However, Dashboard 100 also provides additional sub-categories of data, or sub-metrics, for each of the foregoing top-level metrics 61, 62, 63, 64. Dashboard 100 also includes the graphical representations and data categories seen in FIG. 1, such as Trend 65, Percentile Rank 66, Value Used for Ranking 67, and Prior Rank 68. However, Dashboard 100 also includes additional columns of data for each metric and sub-metric, such as Peer Group 110 and Population 120. Dashboard 100 may also include data for Target Rank 69 (as shown and described with reference to FIG. 1). In an exemplary embodiment, Peer Group 110 informs the user how the organization is being compared (e.g., on a National scale, by Region, or against similar facilities). Population 120 reflects the number of other organizations/entities that are similar to the organization, i.e., the peer groups to which the organization is compared. Thus, for example, Population 120 may reflect the number of hospitals of similar size, or other outpatient facilities, etc. In one embodiment, Population 120 and the peer group that defines the same is set by the administrator of the methods and systems of the present disclosure.

As mentioned, Dashboard 100 includes additional rows of data, or sub-metrics, for each respective top-level metric, and each sub-metric includes data for each of the columnar graphical representations and data categories shown in FIG. 2. For example, Satisfaction 61 includes nine sub-metrics: Satisfaction (Aggregate) 141; HCAHPS 0-10 142; HCAHPS Recommended 143; CGCAHPS 0-10 144; CGCAHPS Recommended 145; Inpatient 146; Emergency 147; Medical Practice 148; and Outpatient 149. Operations 62 includes three sub-metrics: Operations (Aggregate) 151; ALOS 152; and Average Cost of Care 153. Quality-Outcomes 63 includes three sub-metrics: Outcomes (Aggregate) 161; Risk-Adjusted Inpatient Mortality Index (RAMI) 162; and The Composite Patient Safety Index 163. And Quality-Process 64 includes five sub-metrics: Process (Aggregate) 171; Acute MI 172; CHF 173; Pneumonia 164; Surgical Care 175. To the extent data is available, each of these sub-metrics includes data for each of the columnar graphical representations and data categories 65, 66, 67, 68, 69, 110, and 120.

Each top-level metric in FIG. 2 is also a hotlink. However, in one embodiment of the present disclosure, only the Satisfaction metric 61 will take the user to a new functional screen without the need for additional products or software. For example, if a user selects Satisfaction 61 shown in FIG. 2, the user will be directed to a new screen which displays the Satisfaction Dashboard 200 (discussed in more detail below with regard to FIG. 3). And the user will be taken to the Satisfaction Dashboard 200 without needing to purchase or download additional software or programming. Thus, in one embodiment, Operations 62, Quality-Outcomes 63, and Quality-Process 64 are integrated together yet separate from Satisfaction 61. However, in another embodiment, Satisfactions 61 may be linked to, and integrated with, Operations 62, Quality-Outcomes 63, and Quality-Process 64.

Each top-level metric includes an "Aggregate" sub-metric (e.g., 141, 151, 161, and 171), each representing the organization's rank for a particular top-level metric. The Percentile Rank 66 for each Aggregate 141, 151, 161 and 171, represented by a colored circle, is the organization's rank, and is calculated by averaging the mean ranks for each sub-metric below. For example, the Satisfaction-Aggregate 141 for percentile rank is the average of the mean values of the 8 percentile ranks below (i.e., the mean value of the percentile rank for the following: HCAHPS 0-10 142, HCAHPS Recommended 143, CGCAHPS 0-10 144, CGCAHPS Recommended 145, Inpatient 146, Emergency 147, Medical Practice 148, and Outpatient 149). The same is true for Operations 62, Quality-Outcomes 63 and Quality-Process 64. Additionally, for Performance Dashboard 100, the aggregate value of the Percentile Rank for each metric is represented by a color-coded circle enclosing an arrow. These circles are what appear on the dart chart 50 shown in FIG. 2, which is the same dart chart 50 shown in FIG. 1.

Each sub-metric for each of Satisfaction 61, Operations 62, Quality-Outcomes 63, and Quality-Process 64 represents a specific set of information. For instance, several of the sub-metrics represent calculations of survey data, whereas other sub-metrics represent calculations based on publically available data. The "Value Used for Ranking" 67 column represents the key calculation for each sub-metric. And the Value Used for Ranking 67 calculation is unique for each sub-metric. In addition, the Value Used for Ranking 67 is the basis for the percentile rank 66 calculation, both of which are discussed in more detail below.

Referring still to FIG. 2, Operations 62 includes three sub-metrics: Operations Aggregate 151; ALOS 152; and Average Cost of Care 153. As previously discussed, Operations Aggregate 151 is the aggregate value of the ALOS 152 and Average Cost of Care 153 across certain of the columnar data calculations (e.g., 66, 67, and 68). In this exemplary embodiment, only some of the columnar data calculations and graphical representations will require a true aggregate sum of the sub-metrics data. For example, Population 110 is the same for each sub-metric. The Value Used for Ranking column 67 in ALOS 152 (Average Length of Stay) represents a organization's actual ALOS for each patient, or client, compared to a case-mix and severity-adjusted mean expected value from the MedPAR population. The Value Used for Ranking 67 is then used to calculate the organization's percentile rank 66.

The Value Used for Ranking column 67 in the Average Cost of Care 153 sub-metric represents the average cost per patient per stay. For example, if the organization is a hospital, this metric calculates the average cost to the hospital for providing care to a patient. First, this metric totals all the charges by department—i.e., sums the charges made from the hospital to the patient for items used during the patient's stay, and does so on a department-by-department basis. Then using the most recent HCRIS (Healthcare Cost Report Information System), this metric calculates an organization's cost-to-charge ratio. A case-mix and severity-adjusted expected average cost per case is calculated from the MedPAR data, with an additional geographical Wage Index adjustment applied to the benchmarking hospitals. This adjusts relative labor costs in order to match the labor component of the user's overall costs.

Quality-Outcomes 63 also includes three sub-metrics: Outcomes Aggregate 161; Risk-Adjusted Inpatient Mortality Index (RAMI) 162; and The Composite Patient Safety Index 163. As discussed with regard to the previous Aggregate sub-metrics, Outcomes Aggregate 171 is the mean value of its two sub-matrices, RAMI 162 and the Composite Patient Safety Index 163, across each of the appropriate columnar data calculations. RAMI 162 is calculated using MedPAR data and the All Patient Refined Diagnosis Related Groups (APR-DRG) software from 3M™. Inpatient mortality data is determined from MedPAR and then fed through the APR-DRG software (which may be operated using the internet). In this embodiment, the two most recent quarters of data are used to calculate the score. Composite Patient Safety Index 163 is determined by feeding MedPAR data on the organization's cases through software available on the Agency for Healthcare Research and Quality website.

Quality-Process 64 includes five sub-metrics: Process Aggregate 171; Acute MI 172; CHF 173; Pneumonia 174; and Surgical Care 175. As discussed with regard to the previous Aggregate sub-metrics, Process Aggregate 171 is the mean of its sub-matrices. Process sub-matrices 172, 173, 174 and 175, for companies or organizations that are hospitals, are determined from hospital process data from the CMS Hospital Compare website. In this embodiment, the two most recent quarters of data are used to calculate the score. Companies or organizations that are hospitals are ranked directly by score.

Referring still to FIG. 2, Satisfaction 61 consists of eight sub-metrics in addition to Satisfaction Aggregate 141, including: HCAHPS 0-10 142, HCAHPS Recommended 143, CGCAHPS 0-10 144, CGCAHPS Recommended 145, Inpatient 146, Emergency 147, Medical Practice 148, and Outpatient 149. As with each of the top-level metrics 61, 62, 63, and 64, it should be understood that the sub-matrices provided are exemplary only, and that additional sub-matrices may be available. There are two options for determining the Value Used for Ranking for the Satisfaction metric. In one embodiment, the default may be set so that the mean of CAHPS data 142, 143, 144, and 145 is used. Dashboard 100 as shown in FIG. 2 used this method for calculating the aggregate Value Used for Ranking. In another embodiment (not shown), the aggregate Value Used for Ranking may be calculated by taking the mean of Inpatient 146, Emergency 147, Medical Practice 148 and Outpatient 149. Each method is described in more detail below.

CAHPS 0-10 142, CAHPS Recommended 143, CGCAHPS 0-10 144 and CGCAHPS Recommended 145 may be calculated using publically available data from the United States government's CAHPS system. Alternatively, 142, 143, 144, and 145 may be calculated using a CAHPS system implemented by the administrator of the method and systems of the present disclosure. Regardless of the source of the data used to calculate CAHPS 142, 143, 144, and 145, in one embodiment, a minimum of thirty CAHPS questionnaires is required for a particular time period in order to use the CAHPS measurements 142, 143, 144, and 145 to calculate the Value Used for Ranking.

Survey data is used to calculate Inpatient 146, Emergency 147, Medical Practice 148, and Outpatient 149. For example, if the organization is a hospital, the organization will send surveys to patients who recently received healthcare. Thus, for example, the organization will send Inpatient surveys like the one seen in FIG. 5 to persons who were inpatients at the organization's facility. In one embodiment, the organization sends paper surveys to its patients. In another embodiment, phone interview surveys may be conducted. In yet another embodiment, online surveys may be filled out. The organization may direct the survey responses directly to the administrator of the methods and systems of the present disclosure. Once the administrator has the data, the data is then used to calculate the Value Used for Ranking 67 for the appropriate sub-metric.

TABLE 1

| | | | | Valued Used for Ranking | | | | | | | | | |
|---|---|---|---|---|---|---|---|---|---|---|---|---|---|
| Patient | A1 | A2 | A3 | Section A | B1 | B2 | B3 | B4 | Section B | C1 | C2 | Section C | Overall |
| 1 | 100 | 75 | 100 | 91.7 | 25 | 75 | 100 | 25 | 56.3 | missing | 75 | 75.0 | 74.3 |
| 2 | 75 | 50 | 50 | 58.3 | 50 | 50 | 75 | 25 | 50.0 | 75 | 75 | 75.0 | 61.1 |

TABLE 1-continued

| | | | | Valued Used for Ranking | | | | | | | | | |
|---|---|---|---|---|---|---|---|---|---|---|---|---|---|
| Patient | A1 | A2 | A3 | Section A | B1 | B2 | B3 | B4 | Section B | C1 | C2 | Section C | Overall |
| 3 | missing | 75 | 75 | 75.0 | 75 | 25 | 75 | 50 | 56.3 | 75 | 75 | 75.0 | 68.8 |
| 4 | 50 | 50 | 100 | 66.7 | 75 | missing | 50 | 75 | 66.7 | 50 | 50 | 50.0 | 61.1 |
| 5 | 50 | 75 | 100 | 75.0 | 50 | 75 | 25 | 50 | 50.0 | 75 | 50 | 62.5 | 62.5 |
| n = 5 | | | | 73.3 | | | | | 55.8 | | | 67.5 | 65.6 |

Table 1 is an exemplary table used to calculate the Value Used for Ranking 67 for each of the sub-metrics under Satisfaction 61 (except for the CAHPS sub-metrics 142, 142, 144, and 145), and is used in conjunction with a survey that corresponds to each sub-metric, such as the exemplary survey in FIG. 5.

In this exemplary embodiment, assuming the user is a hospital, the first column on the left indicates the number of patients who responded to a given survey. Each column between the Patient column and the Section A column corresponds to a set of questions given on a particular survey. That is, each survey categorizes questions by letter. For example, FIG. 5 is an example of questions used in an Inpatient survey 400. The first set of questions is: "A. Admission" 410, with two questions provided below (412 and 414) and places for written comments 416. Accordingly, in a table like the exemplary table shown in Table 1, question 412 would correspond to column "A1," and question 414 would correspond to column "A2" column. This same pattern would be followed for all categories in the Inpatient survey. Thus, Table 1 reflects a survey that has three categories of questions (A-C) with three questions for categories A and C, and two questions for category B.

In the exemplary survey shown in FIGS. 5A and 5B, a patient is presented with five answer options, ranging from "1 very poor" to "5 very good" (401).

Once all question responses are input into a table such as exemplary Table 1, the patient-level mean values for each section are calculated, as reflected in columns "Section A," "Section B," and "Section C." The method for calculating the mean scores for each section is on a patient-by-patient basis. In this method, the Section A score for Patient 1 is calculated by adding together the total value of Patient 1's responses for that section (as shown in Table 1, that would be 100+75+100) and then dividing that sum by the number of questions in that section that the patient responded to (which is three for section A). As shown in Table 1, Patient 1 had a Mean Section Score for Section A of 91.7. This same process is then repeated for all patients "n" who responded to the survey (in Table 1, n=5), for all the sections. Each patient's overall mean score, shown in the far right "Overall" column, is calculated similarly. This is done by taking a mean of the patient's non-missing mean section scores (e.g., for Patient 1 in Table 1, this would be done by adding 91.7+56.3+87.5 and then dividing that sum by 3).

Once all patient-level values are calculated, facility-level mean values can be determined. The facility-level mean score for the responses of patients 1-5 to question A1 can be calculated by adding together each patient's answer and then dividing by the number of patients who responded to that item (e.g., (100+75+50+50)/4=70). The facility-level mean section scores are calculated similarly by adding together each patient's section score and then dividing by the number of patients who had at least one non-missing response to an item in that section (e.g., Section A=(91.7+58.3+75.0+66.7+75.0)/5=73.3). Note that calculating the facility-level mean section score by adding together the mean facility-level question scores and dividing by the number of non-missing facility-level items scores will not necessarily result in the same value as the previously described method.

The facility-level Overall Mean Score (as shown in Table 1 is 65.6) is the Value Used for Ranking 67 for each sub-metric. The facility-level Overall Mean Score is calculated on a patient-by-patient basis. This can be done by adding together each patient's overall mean score and then dividing by the number of patients with non-missing patient-level overall mean scores (e.g., (74.3+61.1+68.8+61.1+62.5)/5). Note that calculating the facility-level overall mean score by adding together the mean facility-level section scores and dividing by the number of non-missing facility-level section scores will not necessarily result in the same value as the previously described method.

As mentioned, the facility-level Overall Mean Score is equal to the Value Used for Ranking 67 for each sub-metric. And as also mentioned above, the Value Used for Ranking 67 for each sub-metric is necessary in order to determine the Percentile Rank 66 for each sub-metric (and thus ultimately the Aggregate Percentile Rank 141, 151, 161, and 171). The methods and systems of the present disclosure may use one of two different equations to calculate the Percentile Rank 66.

$$PR = 100 - [(50 \times ((2 \times G) + T)) \div N] \quad (I)$$

or $$PR = [(L + (T \div 2)) \div N] \times 100 \quad (II)$$

In equation (I): PR=Percentile Rank; G=the number of facilities with scores greater than the organization's Value Used for Ranking; T=the number of facilities with scores tied with the organization's Value Used for Ranking; and N=the total number of facilities in the peer group. In order to determine G and T, the administrator of the methods and systems of the present disclosure compares the organization's Value Used for Ranking to other known Values for other organizations of the present disclosure, all of which are maintained in a proprietary database. Both G and T, however, are also a function of N, as they are determined relative to the selected peer group N. The peer group N may be determined by the administrator of the methods and systems of the present disclosure.

In equation (II): PR, T, and N are the same, with the only different being L=the number of facilities with scores lower than the organization's Value Used for Ranking. Thus, equation (I) compares the organization's Value Used for Ranking to those peers whose Values are higher while equation (II) compares the organization's Value Used for Ranking to those peers whose Values are lower.

The actual calculation of the Percentile Rank is the same regardless of the equation used. For example, assume N=100, and that 20 facilities have a value higher than the user's Value (G=20), that 10 facilities are tied with the user (T=10) and thus that 70 facilities have a value less than the organization's Value (L=70). Equation (I) is as follows:

$$PR=100-[(50\times((2\times20)+10))\div100]$$

$$PR=100-[(50\times(40+10))+100]$$

$$PR=100-[2500\div100]=75$$

Equation (II) is as follows:

$$PR=[(70+(10\div2))\div100]\times100$$

$$PR=[(70+(5))\div100]\times100$$

$$PR=0.75\times100=75$$

The Percentile Rank 66 is calculated for each sub-metric (141-147, 151-153, 161-165, and 171-173) of each of the top-level metrics Satisfaction 61, Operations 62, Quality-Process 63 and Quality-Outcomes 64. Once the Percentile Rank has been determined for each sub-metric, the mean of those Percentile Ranks is then determined to calculate the Aggregate score for each top-level metric (141, 151, 161, and 171). Referring to FIG. 2, for illustrative purposes only, the aggregate percentile ranks are: Satisfaction (Aggregate) 141=75; Operations (Aggregate) 151=43; Process (Aggregate) 161=86; and Outcomes (Aggregate) 171=88. As previously mentioned, and as can be seen with reference to FIG. 2, these are the same values that appear on the dart chart 50. It should be noted that, in this embodiment, Satisfaction (Aggregate) 141 was calculated by finding the mean value of the CAHPS 0-10 142 and CAHPS Recommended 143 sub-matrices.

If a user chooses to focus specifically on one of the top-level metrics such as Satisfaction 61, for example, then the user would proceed by clicking the Satisfaction 61 hotlink. Upon doing so, the user will be taken to a webpage like that shown in FIG. 3.

Figure 3:
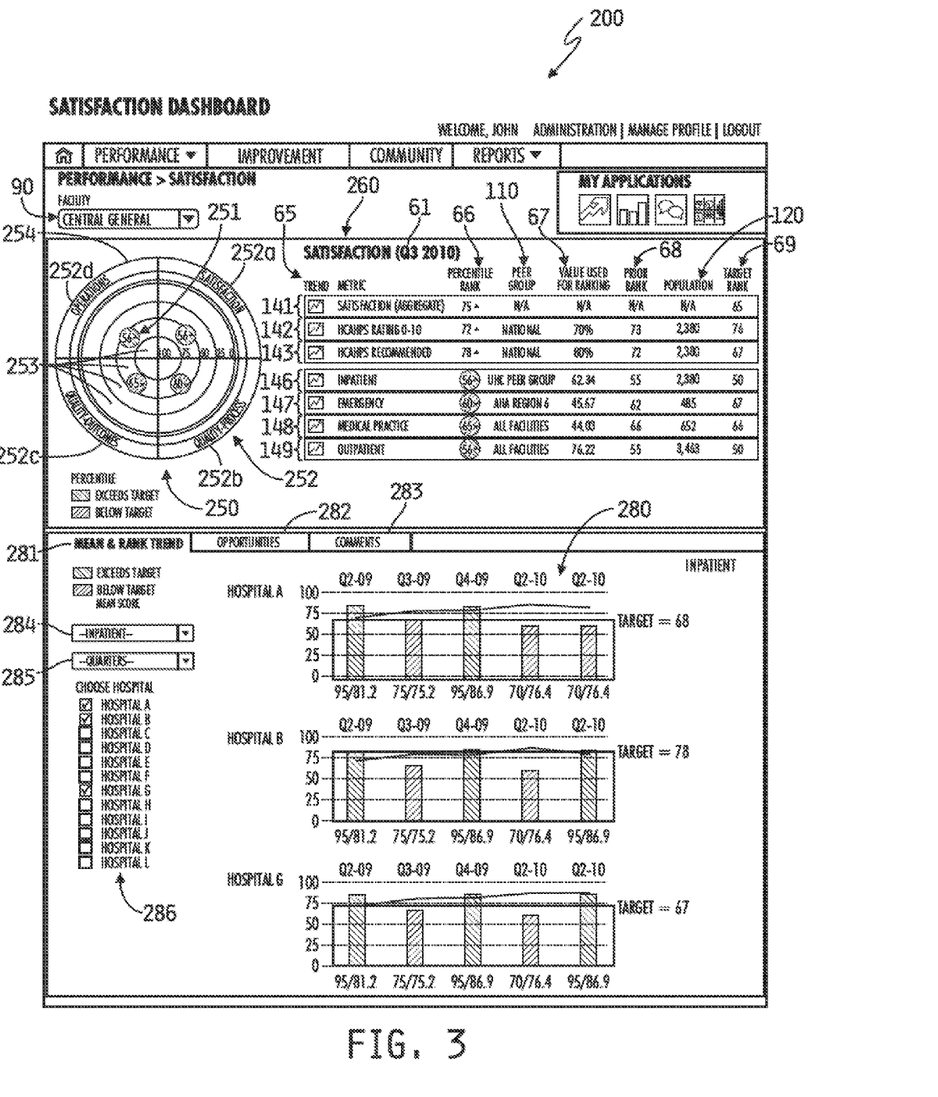
FIG. 3 depicts a screenshot of an exemplary satisfaction dashboard.

The Satisfaction Dashboard 200 shown in FIG. 3 is similar to the Performance Dashboard 100 in FIG. 2. However, Satisfaction Dashboard focuses solely on the Satisfaction top-level metric 61. In doing so, a new dart chart and new performance chart are provided—Satisfaction Dart Chart 250 Satisfaction Performance Chart 260. The overall configuration of Satisfaction Dart Chart 250 is similar to dart chart 50 from FIGS. 1 and 2, except the four quadrants 252*a-d* in the Satisfaction Dart Chart 250 reflect percentile ranks from each of the sub-metrics of only the Satisfaction top-level metric 61 (as opposed to the quadrants being labeled according to and consistent with all four top-level metrics, 61, 62, 63, and 64). Thus, in this embodiment, Satisfaction Dart Chart 250 includes four quadrants: Outpatient 252*a*; Emergency 252*b*; Medical Practice 252*c*; and Inpatient 252*d*. Outpatient 252*a* corresponds to sub-metric 149. Emergency 252*b* corresponds to sub-metric 147. Medical Practice 252*c* corresponds to sub-metric 148. And Inpatient 252*d* corresponds to sub-metric 146. In an alternative embodiment (not shown), Dart Chart 250 may include only two halves, each corresponding to sub-metric CAHPS 0-10 142 and CAHPS Recommended 143. In yet another embodiment (not shown), Dart Chart 250 may include six sections, each corresponding to the foregoing sub-metrics.

Also similar to dart chart 50, Satisfaction dart chart 250 is divided into quartiles 253, each delineated by values ranging from 0 to 100 (0, 25, 50, 75, and 100). Dart chart 250 also includes circular representations 251 that, this embodiment, correspond to the percentile rank 66 for each sub-metric 146-149. Dart chart 250 also includes outer ring 254 that may be color-coded consistent with the circular representations that appear in each quadrant.

Additionally, like the performance chart in FIGS. 1 and 2, Satisfaction Performance Chart 260 includes columnar graphical representations and data calculations, including Trends 65, Percentile Rank 66, Value Used for Ranking 67, Prior Rank 68, Target 69, Peer Group 110, and Population 120. These graphical representations and calculations are used in the same manner as previously described with regard to FIG. 2, except these focus specifically on data and graphs for the Satisfaction metric 61.

FIG. 3 also includes a tabulated section 280. Section 280 includes three tabs: Mean and Rank Trend 281; Opportunities 282; and Comments 283. The user may select any of the three tabs 281, 282, or 283, by clicking on the same. In addition, section 280 includes Dropdown 284, Dropdown 285, and Checklist 286. Dropdown 284 allows the user to select a particular sub-metric—which in this exemplary embodiment is the Inpatient sub-metric. Dropdown 285 then allows the user to choose how he wants to view data for the sub-metric chosen in Dropdown 284—which in this exemplary embodiment is on a quarterly basis. Finally, Checklist 286 then allows the user to decide which locations he wants to review, the locations being related to the user's selection in Dataview Dropdown 90—in this exemplary embodiment, the user chose Hospital A, Hospital B, and Hospital G.

In the exemplary embodiment shown in FIG. 3, the user has selected Mean and Rank Trend 281. Mean and Rank Trend 281 provides a graphical representation of the user's selections under Dropdown 284, Dropdown 285, and Checklist 286. Note that each icon for each graph in Mean and Rank Trend 281 is a hotlink. In this embodiment, Mean and Rank Trend 281 displays percentile ranks for each of Hospitals A, B and G, on a quarterly basis, for five quarters. It should be understood that this time period is exemplary only. Also note that, in this exemplary embodiment, the percentile ranks are color coded in the same manner as previously described.

Referring still to FIG. 3, Opportunities 282 and Comments 283, if selected, will display information similar to Improvement Opportunities 40 and Comment Ratings 30, respectively, as discussed above with regard to FIG. 1.

Figure 4:
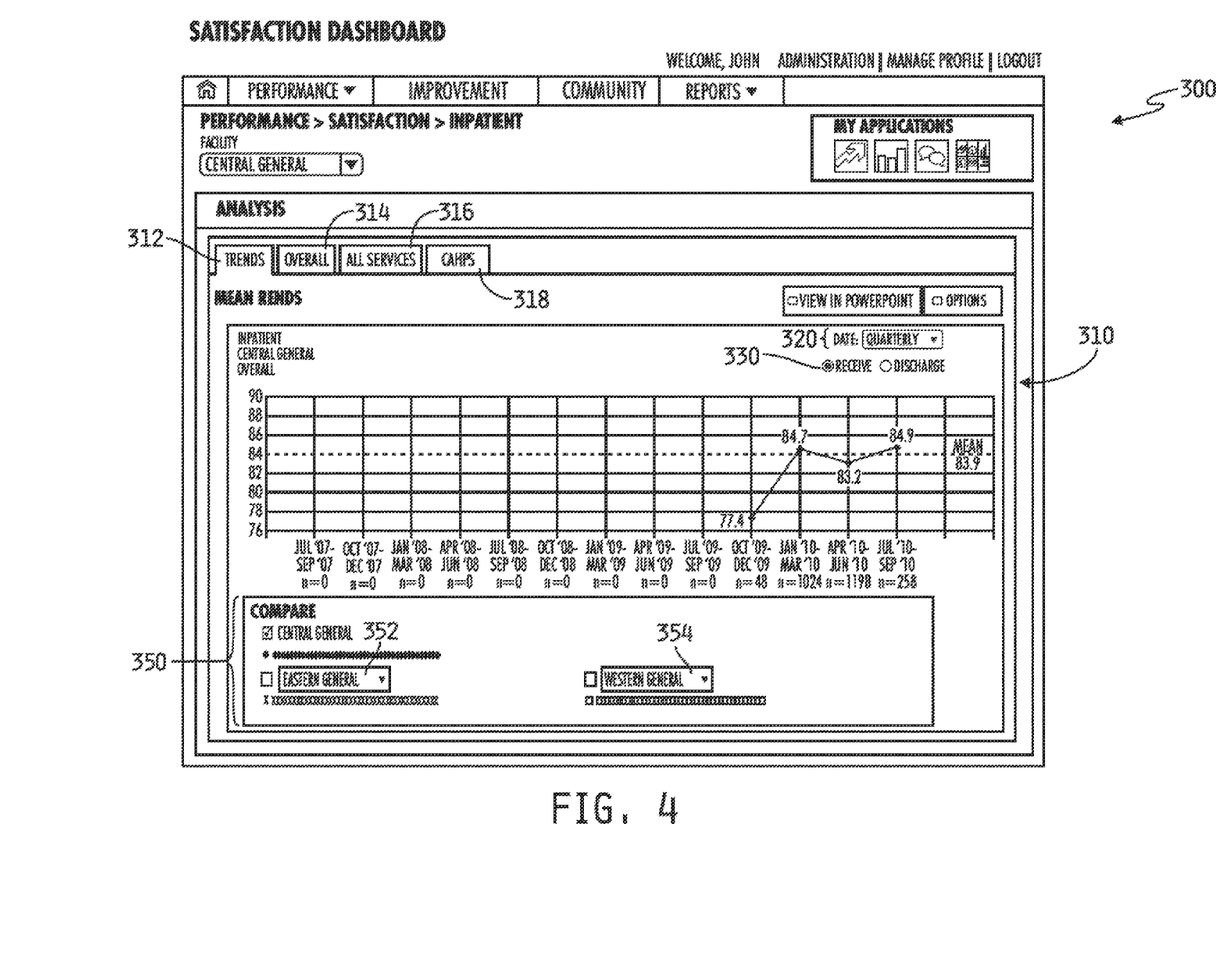
FIG. 4 depicts a screenshot of an exemplary satisfaction analysis graph.

To view a more detailed version of any of the graphical representations from the Mean and Rank Trend 281, the user may simply click the hotlink for the desired graph. Doing so will bring the user to a new webpage 300 similar to the page shown in FIG. 4. In this embodiment, the user selected the Inpatient hotlink from the webpage shown in FIG. 3. In FIG. 4, Satisfaction Analysis Graph 310 is displayed for the Inpatient 144 sub-metric. In this embodiment, Graph 310 includes four additional tabs: Trends 312, Overall 314, All Services 316, and CAHPS 318. Graph 310 may optionally be an flash report, which allows the user to change inputs and outputs without having to reload the page. Thus, the user can change the Date 320 input module to reflect a different time period of performance. The user may also select different datasets by clicking on the "Receive" input module 330 or the "Discharge" input module 340. In addition, bottom portion 350 of Graph 310 includes drop down menus 352 and 354 that allow the user to modify the facility for which the results are shown and optionally compare the same against each other or against the user's performance.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:

1. A user interface displayed on a computer, comprising:
a first graphical representation having a first location and a first plurality of icons located within the first graphical representation, wherein the first plurality of icons display data associated with a user in a first format, and wherein the first graphical representation and the first plurality of icons may be actuated by the user with an input device; and
a second graphical representation having a second plurality of icons located within the second graphical representation, wherein the second plurality of icons display the data associated with the user in a format that is different from the first format, and wherein the second graphical representation and the second plurality of icons may be actuated by the user with an input device;
whereby the first plurality of icons includes a first icon and a second icon, the first icon being located in the first graphical representation at any one of a plurality of locations relative to the first location, a location of the first icon adjacent to the first location indicating the user's performance relative to a first user-defined performance category that is better than the user's performance relative to the first user-defined performance category when the location of the first icon is farther from the first location than the location of the first icon adjacent to the first location, and the second icon being located in the first graphical representation at any one of a plurality of locations relative to the first location, a location of the second icon adjacent to the first location indicating the user's performance relative to a second user-defined performance category that is better than the user's performance relative to the second user-defined performance category when the location of the second icon is farther from the first location than the location of the second icon adjacent to the first location, the second user-defined performance category being different from the first category.

2. The interface of claim 1, wherein the first graphical representation has the appearance of a dart board, and the first location is a center of the dart board.

3. The interface of claim 2, wherein the first graphical representation comprises four quadrants, four quartiles, and an outer ring.

4. The interface of claim 3, wherein at least one of the first plurality of icons is located in each of the four quadrants.

5. The interface of claim 4, wherein the four quadrants, four quartiles, and the outer ring are color coded.

6. The interface of claim 5, wherein the first plurality of icons and the second plurality of icons are color coded.

7. The interface of claim 6, wherein the second graphical representation is a table.

8. The interface of claim 5, wherein the second plurality of icons are color-coded consistent with the color-coding applied to the four quadrants, four quartiles, and the outer ring.

9. The interface of claim 1, wherein the data being displayed is derived from a publically available source.

10. The interface of claim 1, wherein the data being displayed is derived from a private source.

11. The interface of claim 1, wherein the data being displayed is derived from publically available and private sources.

12. The interface of claim 1, wherein actuation of one of the first graphical representation and the second graphical representation causes the interface to display a third graphical representation including additional data related to the actuated graphical representation.

13. A method of providing a user interface, comprising:
allowing a user to login to a website;
providing a first graphical representation having a first plurality of icons located within the first graphical representation, wherein the first plurality of icons display data associated with a user in a first format, and wherein the first graphical representation and the first plurality of icons may be actuated by the user with an input device; and
providing a second graphical representation having a second plurality of icons located within the second graphical representation, wherein the second plurality of icons display the data associated with the user in a format that is different from the first format, and wherein the second graphical representation and the second plurality of icons may be actuated by the user with an input device;
whereby the first plurality of icons includes a first icon and a second icon, the first icon being located in the first graphical representation at any one of a plurality of locations relative to the first location, a location of the first icon adjacent to the first location indicating the user's performance relative to a first user-defined performance category that is better than the user's performance relative to the first user-defined performance category when the location of the first icon is farther from the first location than the location of the first icon adjacent to the first location, and the second icon being located in the first graphical representation at any one of a plurality of locations relative to the first location, a location of the second icon adjacent to the first location indicating the user's performance relative to a second user-defined performance category that is better than the user's performance relative to the second user-defined performance category when the location of the second icon is farther from the first location than the location of the second icon adjacent to the first location, the second user-defined performance category being different from the first category.

14. The method of claim 13, wherein the first graphical representation has the appearance of a dart board, and the first location is a center of the dart board.

15. The method of claim 13, wherein the first graphical representation comprises four quadrants, four quartiles, and an outer ring.

16. The method of claim 15, wherein at least one of the first plurality of icons is located in each of the four quadrants.

17. The method of claim 16, wherein the four quadrants, four quartiles, and the outer ring are color coded.

18. The method of claim 17, wherein the first plurality of icons and the second plurality of icons are color coded.

19. The method of claim 18, wherein the second graphical representation is a table.

20. The method of claim 17, wherein the second plurality of icons are color-coded consistent with the color-coding applied to the four quadrants, four quartiles, and the outer ring.

21. The method of claim 13, wherein the data being displayed is derived from a publically available source.

22. The method of claim 13, wherein the data being displayed is derived from a private source.

23. The method of claim 13, wherein the data being displayed is derived from publically available and private sources.

24. The method of claim 13, wherein actuation of one of the first graphical representation and the second graphical representation causes the interface to display a third graphical representation including additional data related to the actuated graphical representation.

25. A method of providing a user interface, comprising:
maintaining profile information for a user;
providing the user with access to a network;
using the user's profile information to provide a first graphical representation having a first plurality of icons located within the first graphical representation, wherein the first plurality of icons display data associated with a user in a first format, and wherein the first graphical representation and the first plurality of icons may be actuated by the user with an input device; and
using the user's profile information to provide a second graphical representation having a second plurality of icons located within the second graphical representation, wherein the second plurality of icons display the data associated with the user in a format that is different from the first format, and wherein the second graphical representation and the second plurality of icons may be actuated by the user with an input device;
whereby the first plurality of icons includes a first icon and a second icon, the first icon being located in the first graphical representation at any one of a plurality of locations relative to the first location, a location of the first icon adjacent to the first location indicating the user's performance relative to a first user-defined performance category that is better than the user's performance relative to the first user-defined performance category when the location of the first icon is farther from the first location than the location of the first icon adjacent to the first location, and the second icon being located in the first graphical representation at any one of a plurality of locations relative to the first location, a location of the second icon adjacent to the first location indicating the user's performance relative to a second user-defined performance category that is better than the user's performance relative to the second user-defined performance category when the location of the second icon is farther from the first location than the location of the second icon adjacent to the first location, the second user-defined performance category being different from the first category.

26. The method of claim 25, wherein the first graphical representation has the appearance of a dart board, and the first location is a center of the dart board.

27. The method of claim 26, wherein the first graphical representation comprises four quadrants, four quartiles, and an outer ring.

28. The method of claim 27, wherein at least one of the first plurality of icons is located in each of the four quadrants.

29. The method of claim 28, wherein the four quadrants, four quartiles, and the outer ring are color coded.

30. The method of claim 29, wherein the first plurality of icons and the second plurality of icons are color coded.

31. The method of claim 30, wherein the second graphical representation is a table.

32. The method of claim 29, wherein the second plurality of icons are color-coded consistent with the color-coding applied to the four quadrants, four quartiles, and the outer ring.

33. The method of claim 25, wherein the data being displayed is derived from a publically available source.

34. The method of claim 25, wherein the data being displayed is derived from a private source.

35. The method of claim 25, wherein the data being displayed is derived from publically available and private sources.

36. The method of claim 25, wherein actuation of one of the first graphical representation and the second graphical representation causes the interface to display a third graphical representation including additional data related to the actuated graphical representation.

* * * * *